(12) United States Patent
Hess

(10) Patent No.: US 7,319,898 B2
(45) Date of Patent: Jan. 15, 2008

(54) SELF-ADAPTING DEFIBRILLATOR INDUCTION FEATURE

(75) Inventor: Michael F. Hess, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 541 days.

(21) Appl. No.: 10/423,073

(22) Filed: Apr. 25, 2003

(65) Prior Publication Data

US 2004/0215248 A1 Oct. 28, 2004

(51) Int. Cl.
*A61N 1/39* (2006.01)

(52) U.S. Cl. .............................. 607/5; 607/7

(58) Field of Classification Search ............. 607/5, 607/7, 8
See application file for complete search history.

(56) References Cited

U.S. PATENT DOCUMENTS

| | | | |
|---|---|---|---|
| 4,164,946 A * | 8/1979 | Langer | 607/27 |
| 5,105,809 A * | 4/1992 | Bach et al. | 607/5 |
| 5,129,392 A | 7/1992 | Bardy et al. | |
| 5,215,083 A | 6/1993 | Drane et al. | |
| 5,346,506 A | 9/1994 | Mower et al. | |
| 5,395,373 A * | 3/1995 | Ayers | 607/8 |
| 5,564,422 A | 10/1996 | Chen et al. | |
| 5,609,618 A | 3/1997 | Archer | 607/74 |
| 5,643,323 A * | 7/1997 | Kroll et al. | 607/2 |
| 5,649,971 A | 7/1997 | Fain et al. | |
| 5,709,711 A | 1/1998 | Fain | 607/8 |
| 6,047,212 A | 4/2000 | Gliner et al. | |
| 6,345,200 B1 | 2/2002 | Mouchawar et al. | |
| 2003/0130697 A1* | 7/2003 | Halperin et al. | 607/2 |

FOREIGN PATENT DOCUMENTS

| | | |
|---|---|---|
| EP | 0597431 A2 | 5/1994 |
| EP | 0 473 002 B1 | 12/1995 |
| EP | 0 607 637 B1 | 3/1999 |

* cited by examiner

*Primary Examiner*—Angela D. Sykes
*Assistant Examiner*—Michael Kahelin
(74) *Attorney, Agent, or Firm*—Michael C. Soldner

(57) ABSTRACT

A system that includes a programming device and a defibrillator provides a self-adapting defibrillator induction feature to test the effectiveness of the defibrillator in detecting and terminating fibrillation of a heart, such as ventricular fibrillation. A fibrillation induction protocol and values for parameters of the protocol are selected. The defibrillator attempts to induce fibrillation according to the selected protocol and parameter values. Parameter values are modified and new protocols are selected until fibrillation is successfully induced, detected and terminated.

37 Claims, 6 Drawing Sheets

SELF-ADAPTING DEFIBRILLATOR INDUCTION FEATURE

TECHNICAL FIELD

The invention relates to medical devices, and more particularly, to medical devices for defibrillating hearts.

BACKGROUND

An implanted device, such as a defibrillator, for example, detects ventricular fibrillation, and delivers one or more electrical pulses to stop the fibrillation and allow the heart to reestablish a normal sinus rhythm. In general, implantable defibrillators deliver a first pulse at a first energy level upon detecting fibrillation and, if the fibrillation is not stopped, deliver additional pulses at increasing energy levels until the fibrillation is stopped or the programmed progression of pulses has been exhausted.

It is generally required that the effectiveness of a defibrillator in ending episodes of fibrillation be confirmed during implantation. Any changes to the configuration and programming of the defibrillator necessary to assure its effectiveness are made at this time. For example, the energy levels or waveforms of pulses delivered by the defibrillator, the sensitivity of the device to detect ventricular fibrillation, or the position of the electrodes used to deliver the pulses, can be changed as necessary to assure the effectiveness of the defibrillator.

The process of confirming the effectiveness of a defibrillator can be time consuming and labor intensive. Typically, a physician or clinician programs the defibrillator to execute an initial fibrillation detection algorithm, and programs an initial progression of defibrillation pulses to be delivered in response to a detected fibrillation. The clinician then programs the defibrillator to induce the heart to fibrillate, so that the programmed detection algorithm and pulse progression can be tested.

The defibrillator induces fibrillation by delivering a pulse during the period of vulnerability within a cardiac cycle, e.g., during or near the T-wave, delivering a high frequency pulse train, delivering direct current, or other known methods for inducing fibrillation. The clinician programs the parameters for the induction attempt, such as the timing, amplitude, or other characteristics of a T-wave shock. If the induction attempt fails, the clinician must program new parameters for another induction attempt. When an induction attempt succeeds, the defibrillator can fail to detect the fibrillation, or fail to stop the fibrillation. In such cases, the clinician must modify the detection algorithm or the pulse progression. The process repeats until successful fibrillation induction, detection, and defibrillation occur such that the effectiveness of the defibrillator is confirmed.

SUMMARY

In general, the invention is directed to techniques for automating portions of the process of inducing fibrillation to test a defibrillator. In particular, the invention is directed to a self-adapting fibrillation induction feature. One or both of a programming device and an implanted defibrillator can provide the self-adapting fibrillation induction feature. A user activates this defibrillator induction feature via the programming device, which communicates with the defibrillator. In some of the embodiments, the user can activate the defibrillator induction feature by entering a single command via the programming device.

A fibrillation induction protocol, such as T-wave shock, high-frequency pulse-train, or direct current delivery, and values for parameters of the protocol are selected. The defibrillator attempts to induce fibrillation according to the selected protocol and parameter values. If fibrillation induction is unsuccessful, parameter values are modified and new protocols are selected until fibrillation is successfully induced. Unsuccessful induction can be defined either as lack of any arrhythmia inducement (maintains sinus rhythm), or induction of a less lethal ventricular tachycardia.

If an induced fibrillation is not detected, a fibrillation detection algorithm is modified. Verification of correct defibrillator detection can be accomplished by the programmer using surface electrogram signals in conjunction with telemetered information from the defibrillator. If an induced fibrillation is detected, it is treated according to a defibrillation therapy progression. The therapy progression can include a first pulse that is a safety margin below the maximum output of the defibrillator, and a second pulse at maximum output. If the first pulse terminates the fibrillation, the test is satisfied and the defibrillator is programmed for permanent operation. If the first pulse fails to terminate the fibrillation, a user can be prompted to change the configuration of the defibrillator or the values for parameters of defibrillation pulses. If the progression fails to terminate the fibrillation, a user is alerted so that the patient can be manually defibrillated. The alert may be provided by activating an alarm.

The user can activate the defibrillator induction feature more than one time for a single patient, for example, to establish and then confirm the effectiveness of the defibrillator in detecting and treating fibrillation. For example, depending on the size of the safety margin or the magnitude of the first pulsed, the user may decide that it would be appropriate to have two successful terminations of ventricular fibrillation before deciding that the defibrillator is effective.

In one embodiment, the invention is directed to a method in which a fibrillation induction protocol and a value for a parameter of the fibrillation induction protocol are automatically selected. An attempt is made to induce fibrillation according to the selected protocol and parameter value. Whether fibrillation was induced according to the selected protocol and parameter value is determined, and the parameter value is modified based on the determination.

In another embodiment, the invention is directed to device that includes a memory to store information relating to a plurality of fibrillation induction protocols, and a processor. The processor selects one of the fibrillation induction protocols and a value for a parameter of the fibrillation induction protocol based on the information, and controls a defibrillator to attempt to induce fibrillation according to the selected protocol and parameter value. The processor determines whether fibrillation was induced according to the selected protocol and parameter value, and modifies the parameter value based on the determination. The device can be the defibrillator or a programming device.

In another embodiment, the invention is directed to a computer-readable medium containing instructions. The instructions cause a programmable processor to select a fibrillation induction protocol and a value for a parameter of the fibrillation induction protocol, and control a defibrillator to attempt to induce fibrillation according to the selected protocol and parameter value. The instructions further cause a programmable processor to determine whether fibrillation was induced according to the selected protocol parameter value, and modify the parameter value based on the determination.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
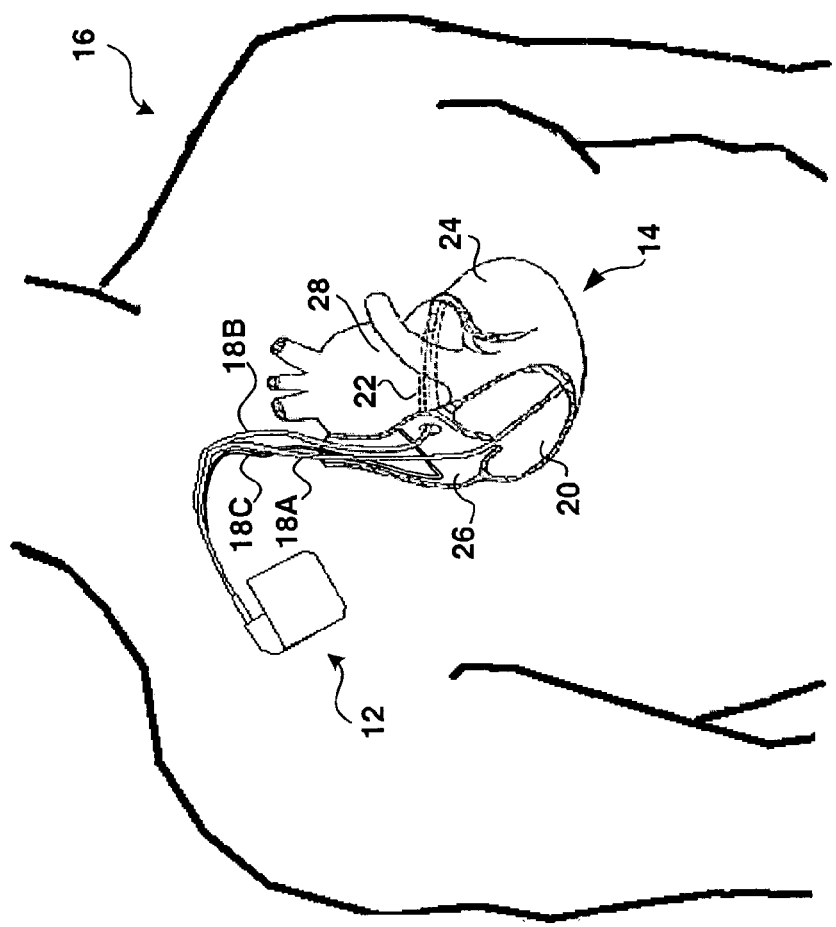
FIG. 1 is a conceptual diagram illustrating an example system that includes an implanted defibrillator and a programming device, and that provides a self-adapting defibrillator induction feature according to the invention.
Figure 1:
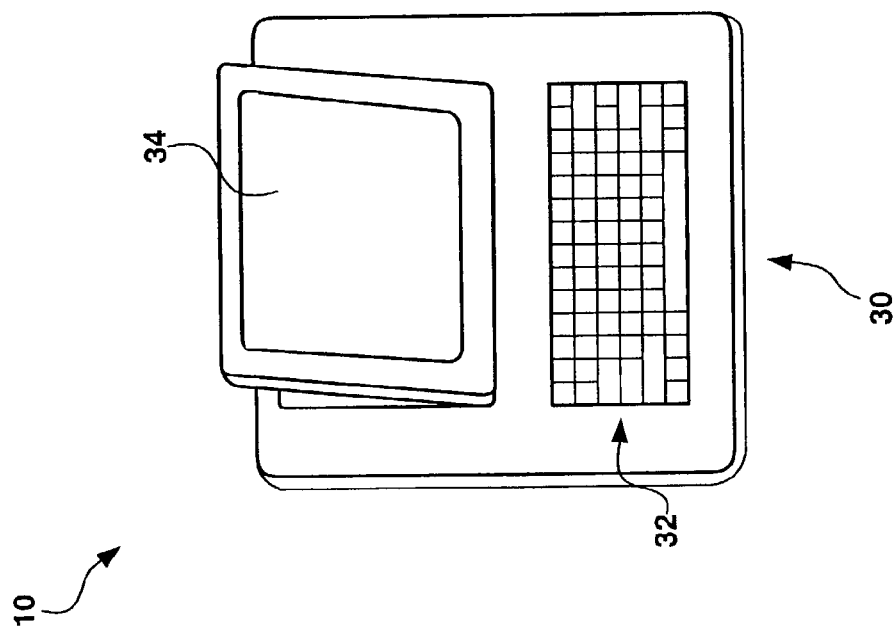

FIG. 1 is a conceptual diagram illustrating an example system 10 that includes an implanted defibrillator 12 and a programming device 30. As will be described, in accordance with the invention, system 10 provides a self-adapting defibrillator induction feature. A user (not shown), such as a physician or clinician, uses the self-adapting defibrillator induction feature to test the effectiveness of defibrillator 12 in treating fibrillations of a heart 14 of a patient 16. The self-adapting defibrillator induction feature can simplify the process of testing the effectiveness of defibrillator 12 from the perspective of the user.

In the example of FIG. 1, defibrillator 12 takes the form of a multi-chamber cardiac pacemaker-cardioverter-defibrillator (PCD) implanted within patient 16. Defibrillator 12 includes leads 18A, 18B and 18C (collectively "leads 18") that extend into the heart 14 of patient 16. More particularly, right ventricular (RV) lead 18A extends through one or more veins (not shown), the superior vena cava, and right atrium 26, and into right ventricle 20. Left ventricular (LV) coronary sinus lead 18B extends through the veins, the vena cava, right atrium 26, and into the coronary sinus 22 to a point adjacent to the free wall of left ventricle 24 of heart 14. Right atrial (RA) lead 18C extends through the veins and vena cava, and into the right atrium 26 of heart 14.

Each of leads 18 includes electrodes (not shown), which defibrillator 12 uses to sense electrical signals attendant to the depolarization and repolarization of heart 14. In some embodiments, defibrillator 12 uses these electrodes to provide pacing pulses to heart 14. The electrodes used by defibrillator 12 for sensing and pacing can be unipolar or bipolar, as is well known in the art.

Defibrillator 12 also provides defibrillation therapy, and in some embodiments provides cardioversion therapy, via electrodes located on leads 14. In some embodiments, electrodes used for defibrillation can also be used for sensing electrical activity of heart 14. Defibrillator 12 detects fibrillation of heart 14, such as fibrillation of ventricles 20 and 24, and delivers defibrillation therapy to heart 14 in the form of electrical pulses. Defibrillator 12 can be programmed to deliver a progression of therapies, e.g., pulses with increasing energy levels, until a fibrillation of heart 14 is stopped. Defibrillator 12 detects fibrillation employing one or more fibrillation detection techniques known in the art.

Defibrillator 12 induces fibrillation of heart 14, e.g., ventricular fibrillation, to test the effectiveness of defibrillator 12 in detecting and stopping the fibrillation. Defibrillator 12 induces fibrillation according to a fibrillation induction protocol, and is capable of employing a plurality of fibrillation protocols to induce fibrillation. Exemplary fibrillation induction protocols include delivery of an electrical pulse to heart 14 during the T-wave of a cardiac cycle, delivery of a high-frequency pulse train, and delivery of direct current. The invention is not limited to the exemplary induction protocols, and defibrillator 12 can induce fibrillation according to any of a number of fibrillation induction protocols known in the art.

The user uses programming device 30 to program defibrillator 12. The user, for example, uses programming device 30 to program a therapy progression, select electrodes used to deliver defibrillation pulses, select waveforms for the defibrillation pulse, select a fibrillation detection algorithm, and the like for the permanent operation of defibrillator 12. The user can also use programming device 30 to program aspects of other therapies provided by defibrillator 12, such as cardioversion or defibrillation therapies.

Prior to completing the implantation and/or permanent programming of defibrillator 12, the user activates the self-adapting defibrillator induction feature provided by system 10 via programming device 30 to test the effectiveness of defibrillator 12 in detecting and treating fibrillation of heart 14. According to the self-adapting defibrillator induction feature, which will be described in greater detail below, one of programming device 30 and defibrillator 12 selects an induction protocol and values of parameters for the induction protocol, and defibrillator 12 attempts to induce fibrillation according to the selected protocol and parameter values. In response to failed attempts to induce fibrillation, the parameter values are modified or a new protocol is selected without user intervention.

The user interacts with programming device 30 and defibrillator 12 via a user interface. In the embodiment illustrated in FIG. 1, the user interface is provided via a keyboard 32 and a monitor 34, which may for example, be a CRT monitor, LCD monitor, LED monitor, or the like. Programming device 30 can additionally or alternatively include a pointing device, such as a mouse, via which a user interacts with the user interface. Programming device 30 communicates with defibrillator 12 via a programming head (not shown) placed over defibrillator 12, and telemetry circuits of defibrillator 12 as is known in the art. In some embodiments, the user activates the self-adapting defibrillator induction feature by entering a single command via programming device 30, such as depression of a single key or combination of keys of keyboard 32 or a single point-and-select action with a pointing device.

The configuration of defibrillator 12 illustrated in FIG. 1 is merely exemplary. Defibrillator 12 can include any number of leads 18, and each of leads 18 can extend to any location within or proximate to heart 14. For example, some embodiments of defibrillator 12 include a single lead 18A or 18C that extends into right ventricle 20 or right atrium 26, respectively, or two leads 18A and 18C that extend into the right ventricle 20 and right atrium 26, respectively. Other embodiments of defibrillator 12 include leads 18A-C located as illustrated in FIG. 1, and an additional lead 18 located within or proximate to left atrium 28.

Some embodiments include epicardial leads and/or patch electrodes instead of or in addition to the transvenous leads 18 illustrated in FIG. 1. Further, defibrillator 12 need not be implanted within patient 16. Where defibrillator 12 is not implanted in patient 16, defibrillator 12 can deliver defibrillation pulses and other therapies to heart 14 via percutaneous leads that extend through the skin of patient 16 to a variety of positions within or outside of heart 14.

Figure 2:
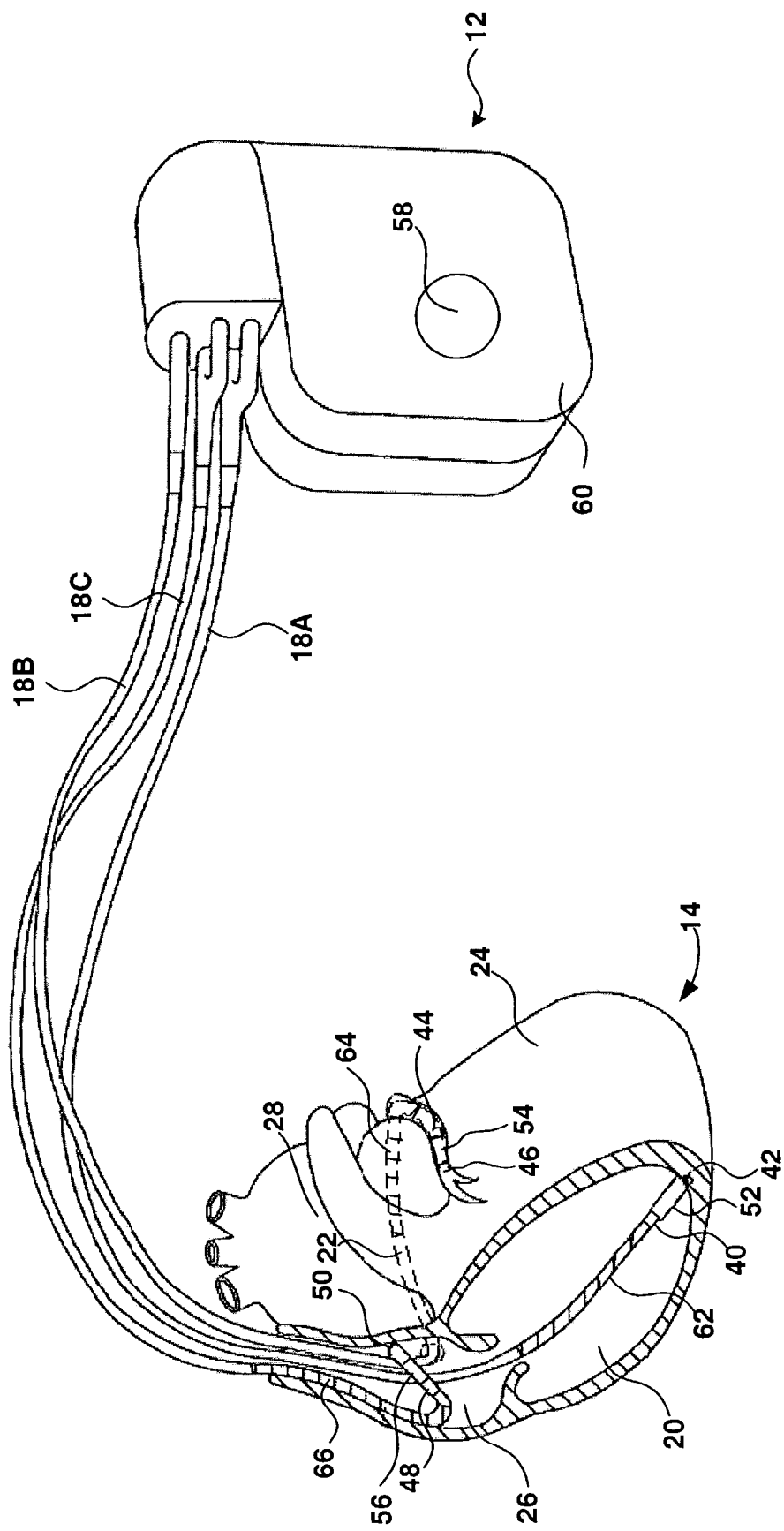
FIG. 2 is a conceptual diagram illustrating the implanted defibrillator of FIG. 1 in greater detail.

FIG. 2 is a conceptual diagram illustrating defibrillator 12 in greater detail. Each of leads 18 includes an elongated insulative lead body carrying a number of concentric coiled conductors separated from one another by tubular insulative sheaths. Located adjacent distal end of leads 18A, 18B and 18C are bipolar electrodes 40 and 42, 44 and 46, and 48 and 50 respectively. Electrodes 40, 44 and 48 can take the form of ring electrodes, and electrodes 42, 46 and 50 can take the form of extendable helix tip electrodes mounted retractably within insulative electrode heads 52, 54 and 56, respectively. Each of the electrodes 40-50 is coupled to one of the coiled conductors within the lead body of its associated lead 18.

Sense/pace electrodes 40, 42, 44, 46, 48 and 50 sense electrical signals attendant to the depolarization and repolarization of heart 14. The electrical signals are conducted to defibrillator 12 via leads 18. In some embodiments, defibrillator 12 also delivers pacing pulses via sense/pace electrodes 40, 42, 44, 46, 48 and 50 to cause depolarization of cardiac tissue. Defibrillator 12 may also include one or more indifferent housing electrodes, such as housing electrode 58, formed integrally with an outer surface of the hermetically sealed housing 60 of defibrillator 12. Any of electrodes 40, 42, 44, 46, 48 and 50 can be used for unipolar sensing or pacing in combination with housing electrode 58.

Leads 18A, 18B and 18C also, as shown in FIG. 2, include elongated coil electrodes 62, 64 and 66, respectively. IMD 10 delivers defibrillation pulses to heart 14 via any combination of defibrillation electrodes 62-66, which can also be combined with housing electrode 58. Electrodes 58 and 62-66 can also be used to deliver cardioversion pulses to heart 14. Defibrillation electrodes 62-66 are fabricated from platinum, platinum alloy or other materials known to be usable in implantable defibrillation electrodes, and may be about 5 cm in length.

Figure 3:
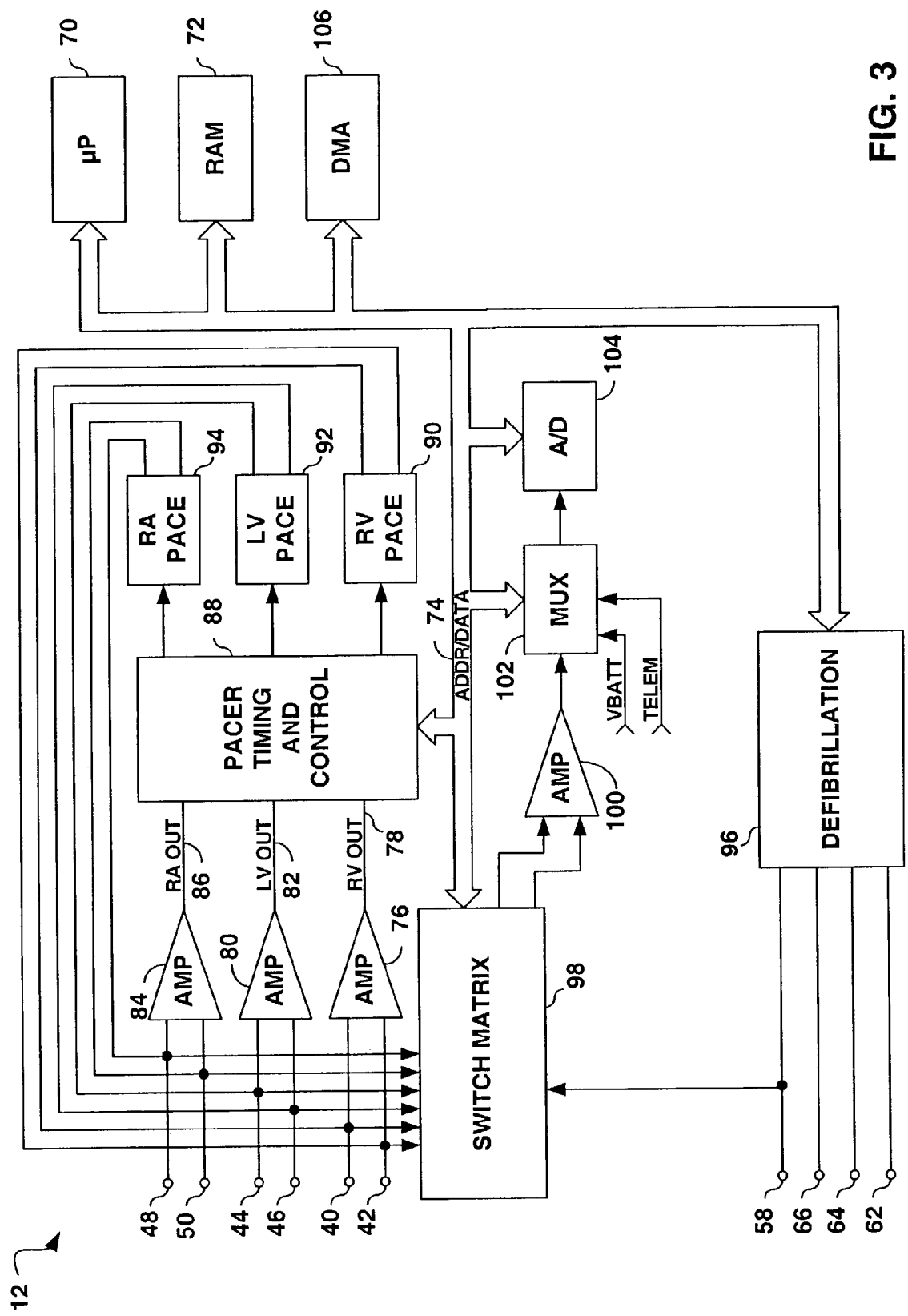
FIG. 3 is a functional block diagram of the implanted defibrillator of FIG. 1.

FIG. 3 is a functional block diagram of defibrillator 12. As shown in FIG. 3, defibrillator 12 can take the form of a multi-chamber PCD having a microprocessor-based architecture. However, this diagram should be taken as exemplary of the type of device in which various embodiments of the present invention may be embodied, and not as limiting.

Defibrillator 12 includes a microprocessor 70. Microprocessor 70 executes program instructions stored in memory, such as a ROM (not shown), EEPROM (not shown), and/or RAM 72, which control microprocessor 70 to perform the functions ascribed to microprocessor 70 herein. Microprocessor 70 is coupled to, e.g., to communicate with and/or control, various other components of defibrillator 12 via an address/data bus 74.

Defibrillator 12 senses electrical activity within heart 14. Electrodes 40 and 42 are coupled to amplifier 76, which can take the form of an automatic gain controlled amplifier providing an adjustable sensing threshold as a function of the measured R-wave amplitude. A signal is generated on RV out line 78 whenever the signal sensed between electrodes 40 and 42 exceeds the present sensing threshold. Thus, electrodes 40 and 42 and amplifier 76 are used to detect intrinsic right ventricular depolarizations.

Electrodes 44 and 46 are coupled to amplifier 80, which also can take the form of an automatic gain controlled amplifier providing an adjustable sensing threshold as a function of measured R-wave amplitude. A signal is generated on LV out line 82 whenever the signal sensed between electrodes 44 and 46 exceeds the present sensing threshold. Thus, electrodes 44 and 46 and amplifier 80 are used to detect intrinsic left ventricular depolarizations.

Electrodes 48 and 50 are coupled to amplifier 84, which can take the form of an automatic gain controlled amplifier providing an adjustable sensing threshold as a function of the measured P-wave amplitude. A signal is generated on RA out line 86 whenever the signal between electrodes 48 and 50 exceeds the present sensing threshold. Thus, electrodes 48 and 50 and amplifier 84 are used to detect intrinsic atrial depolarizations.

In some embodiments, defibrillator 12 paces heart 14. In such embodiments, output circuits 90-94 deliver pacing pulses to heart 14 via electrodes 40-50 under the control of pacer timing/control circuitry 88. Specifically, output circuit 90 is coupled to electrodes 40 and 42 to deliver pacing pulses to right ventricle 20 (FIGS. 1 and 2), output circuit 92 is coupled to electrodes 44 and 46 to deliver pacing pulses to left ventricle 24 (FIGS. 1 and 2), and output circuit 94 is coupled to electrodes 48 and 50 to deliver pacing pulses to right atrium 26 (FIGS. 1 and 2). Output circuits 90-94 include capacitors and switches for the storage and delivery of energy as a pacing pulse, as is known in the art.

Pacer timing/control circuitry 88 preferably includes programmable digital counters which control the basic time intervals associated with modes of pacing. Circuitry 88 also preferably controls escape intervals associated with pacing. Circuitry 88 resets interval counters upon detection of R-waves or P-waves, or generation of pacing pulses, and thereby controls the basic timing of cardiac pacing functions.

Intervals defined by pacing circuitry 88 may also include refractory periods during which sensed R-waves and P-waves are ineffective to restart timing of escape intervals, and the pulse widths of the pacing pulses. The durations of these intervals are determined by microprocessor 70 in response to data stored in RAM 72, and are communicated to circuitry 88 via address/data bus 74. The amplitude of the cardiac pacing pulses is also determined by circuitry 88 under control of microprocessor 70.

Microprocessor 70 operates as an interrupt driven device, and is responsive to interrupts from pacer timing/control circuitry 88 corresponding to the occurrence of sensed P-waves and R-waves and corresponding to the generation of cardiac pacing pulses. Those interrupts are provided via data/address bus 76. Any necessary mathematical calculations to be performed by microprocessor 70 and any updating of the values or intervals controlled by pacer timing/control circuitry 88 take place following such interrupts.

Defibrillator 12 detects ventricular and/or atrial fibrillations of heart 14 using fibrillation detection algorithms known in the art. For example, microprocessor 70 can detect ventricular fibrillation based on R-wave indications received from circuitry 88 by detecting a sustained series of short R-R intervals of an average rate indicative of fibrillation, or an unbroken series of short R-R intervals. Microprocessor 70 can employ single or multiple zone detection techniques.

Defibrillator 12 delivers defibrillation pulses to heart 14 via one or more of electrodes 58, 62, 64 and 66 in response to detected fibrillation. Electrodes 58, 62, 64 and 66, are coupled to a defibrillation circuit 96, which delivers defibrillation pulses under the control of microprocessor 70. Circuit 96 includes energy storage circuits such as capacitors, switches for coupling the storage circuits to electrodes 58, 62, 64 and 66, and logic for controlling the coupling of the storage circuits to the electrodes to create pulses with desired polarities and shapes. Microprocessor 70 may employ an escape interval counter to control timing of defibrillation pulses, as well as associated refractory periods. In some embodiments, microprocessor 70 controls the delivery of cardioversion pulses by defibrillation circuit 96.

Defibrillator 12 delivers stimulation to induce fibrillation of heart 14, e.g., ventricular fibrillation, so that its effectiveness in detecting and stopping fibrillation can be evaluated. Defibrillator 12 is capable of inducing fibrillation of heart 14 according to a plurality of fibrillation induction protocols, such as T-wave shock delivery, high-frequency pulse-train delivery, and direct current delivery protocols known in the art. As will be described in greater detail below, defibrillator 12 attempts to induce fibrillation of heart 14 via a selected induction protocol with selected values for parameters of the protocol, and, according to the self-adapting defibrillation induction feature, attempts to induce fibrillation of heart 14 according to the selected protocol with modified parameter values and then different protocols, until fibrillation is induced.

To induce fibrillation by T-wave shock delivery, processor 70 determines an average intrinsic rate of heart 14 based on R-wave indications received from pacer timing/control circuitry 88, and control circuitry 88 to control pacing via one or more of output circuits 80-84 above the intrinsic rate to provide consistent capture of heart 14. Processor 70 then determines an average interval between delivery of pacing pulses and the occurrence of T-waves within the resulting cardiac cycles, in order time delivery of a pulse during the T-wave.

Specifically, processor 70 controls selection of two or more of electrodes 40-50 and 58 for use in detecting an signal that represents an electrogram (EGM) of heart 14 via switch matrix 98. The signal is amplified and filtered by wideband (0.5-200 Hz) amplifier 100. Analog-to-digital (A/D) converter 104 receives the filtered analog signal via multiplexer 102, and coverts the analog signal to a multi-bit digital, which may be stored in RAM 72 under the control of direct memory access (DMA) circuit 106 for retrieval and digital signal processing by microprocessor 70. Microprocessor 70 detects pacer spikes and T-waves within the EGM to measure the average interval therebetween. In some embodiments, a defibrillator 12 includes a separate digital signal processor (DSP) for digitally processing the signal, and providing the measured intervals or average interval to microprocessor 70.

Using the average interval, and during continued pacing above the intrinsic rate, microprocessor 70 controls defibrillator circuit 96 to deliver a relatively low energy pulse, e.g., less then 5 Joules and preferably between 0.5 and 1.0 Joule, during the T-wave to induce fibrillation. The period of a cardiac cycle during the T-wave represents a period of vulnerability of heart 14 to fibrillation. The energy pulse is delivered via a combination of two or more of electrodes 58 and 62-66. The energy level of the pulse, pulse waveform, timing of delivery of the pulse, and the electrodes used to deliver the pulse are example parameters for the T-wave shock protocol, the values of which can be modified according to the self-adapting defibrillator induction feature in successive attempts to induce fibrillation.

Processor 70 can control delivery of high-frequency pulse-train or direct current via pacer timing/control circuitry 88, one or more of output circuits 80-84, and one or more of electrodes 40-50 to induce fibrillation. Processor 70 can also control delivery of high-frequency pulse-train or direct current via defibrillation circuit and one or more of electrodes 58 and 62-66. Amplitude, frequency, timing and electrodes are examples of modifiable parameters for these protocols.

Figure 4:
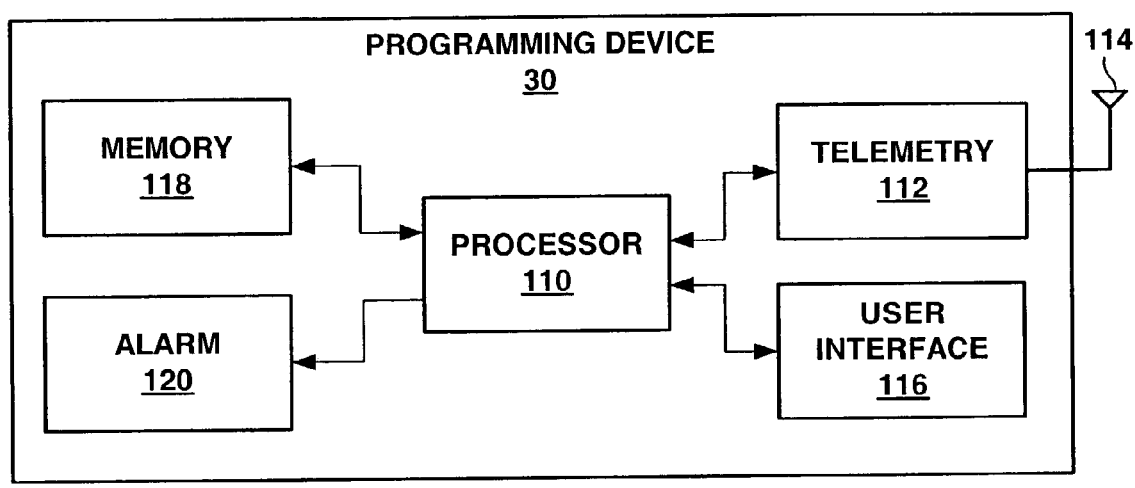
FIG. 4 is a functional block diagram of the programming device of FIG. 1.

FIG. 4 is a functional block diagram of programming device 30. As shown in FIG. 4, programming device 30 includes a processor 110, a telemetry circuit 112, and an antenna 114. As mentioned above, programming device 30 is capable of wireless communication with defibrillator 12. Programming device 30 communicates with defibrillator 12 via telemetry circuit 112 and antenna 114 in order to facilitate provision of a self-adapting defibrillator induction feature according to the invention, as will be described in greater detail below. Antenna 114 can correspond to the programming head that may be placed over heart 14, as described above with reference to FIG. 1.

Programming device 30 provides a user interface 116 by which a user of programming device 30, such as a physician or clinician, interacts with programming device 30 and defibrillator 12. The user interacts with user interface 116 to activate a self-adapting defibrillator induction feature. User interface 116 is a graphical user interface displayed on monitor 34, and a user interacts with user interface 116 via monitor 34, keyboard 32, and/or a pointing device, illustrated in FIG. 1.

Processor 110 provides user interface 116 as described herein. Processor 110 indicates current status of the self-adapting defibrillator induction feature to the user via user interface 116. In some embodiments, programming device 30 indicates an alert situation, e.g., failure of defibrillator 12 to defibrillate an induced fibrillation, by activating an alarm 120.

A memory 118 stores program code that causes processor 110 to provide the functionality ascribed to programming device 30 herein, and information used by processor 110 to provide the functionality ascribed to programming device 30 herein. Memory 118 can include any fixed or removable magnetic, optical, or electrical media, such as RAM, ROM, CD-ROM, hard or floppy magnetic disks, EEPROM, or the like. Processor 110 can take the form one or more microprocessors, digital signal processors (DSPs), application specific integrated circuits (ASICs), field programmable gate arrays (FPGAs), programmable logic circuitry, or the like.

Figure 5A:
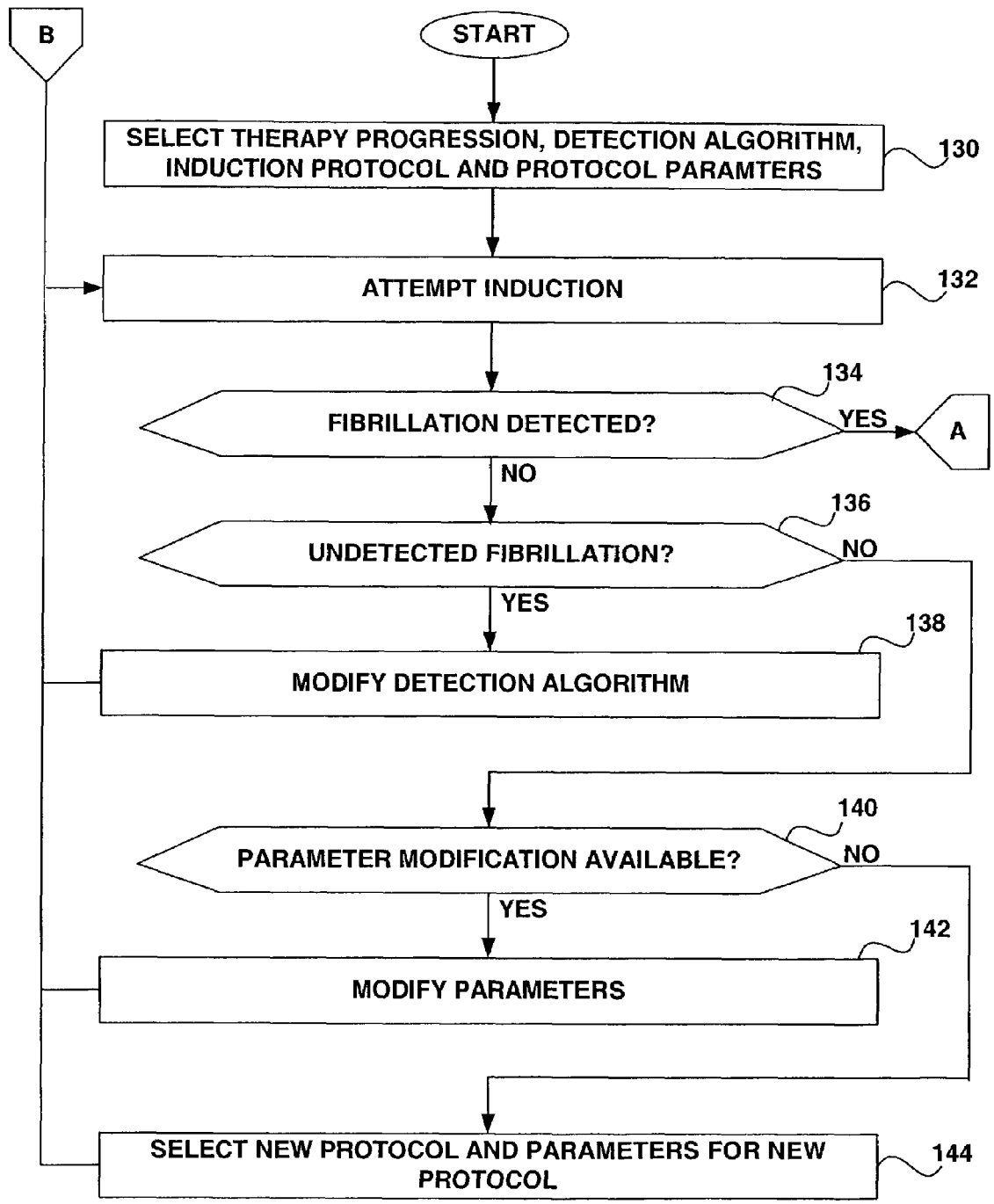
FIGS. 5A-B are flowcharts illustrating an exemplary operation of a self-adapting defibrillator induction feature according to the invention.
Figure 5B:
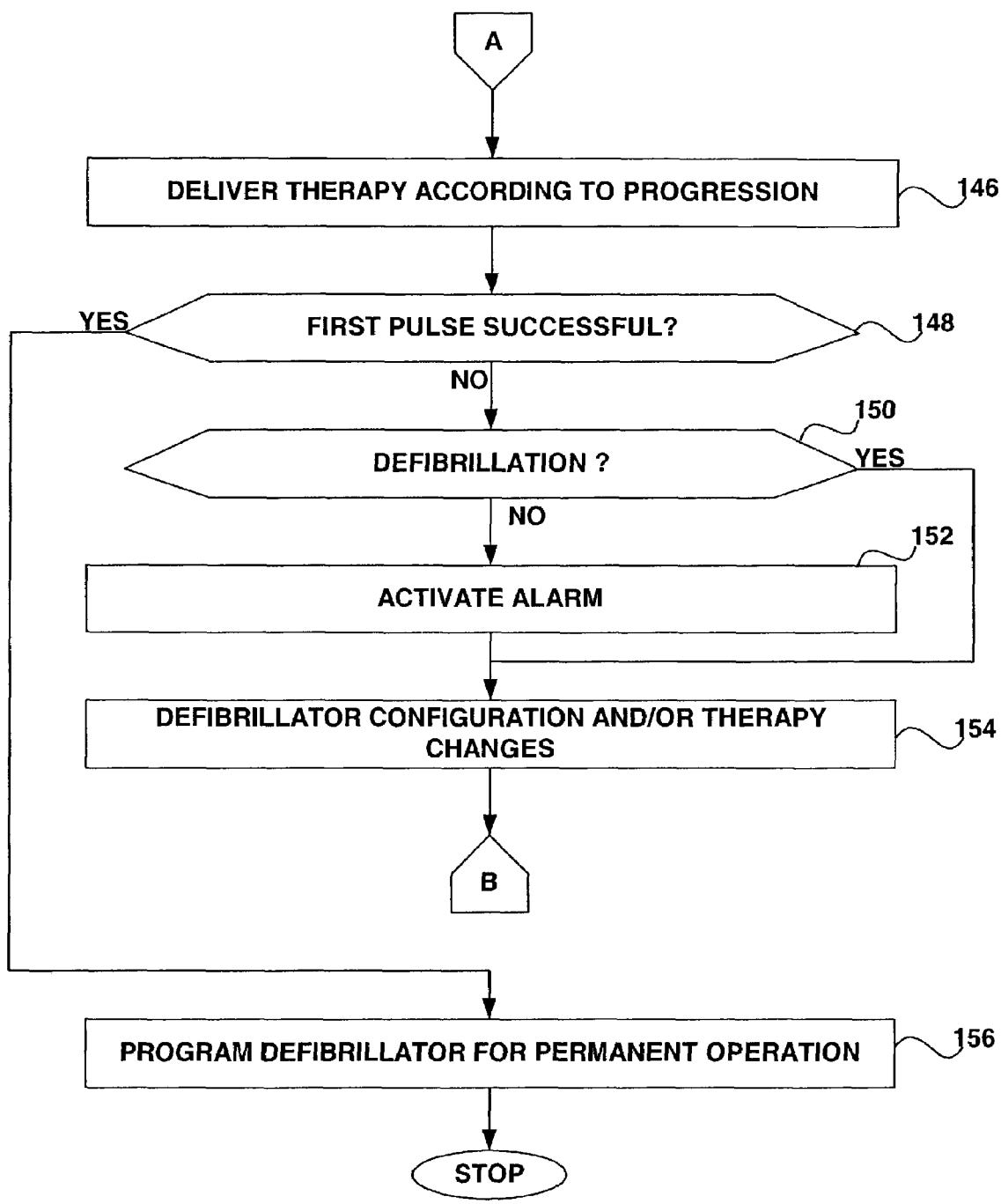

FIGS. 5A-B are flowcharts illustrating an exemplary operation of a self-adapting defibrillator induction feature according to the invention. The various functions that are described below as being performed during operation of a self-adapting defibrillator induction feature can be performed by programming device 30, defibrillator 12, or a combination thereof. For example, in some embodiments, programming device 30 controls the operation of the self-adapting defibrillator induction feature, e.g., selects and modifies fibrillation induction protocols, while defibrillator 12 responds to programming provided by programming device 30 to deliver stimulation to attempt fibrillation induction according to protocols and parameter values selected by programming device 30, and to provide feedback regarding success of fibrillation induction and defibrillation. In other embodiments, defibrillator 12 controls the operation of the self-adapting defibrillator induction feature, receiving a request to activate the feature from a user via programming device 30, and providing status information to the user via programming device 30. For ease of description, the example operation of a defibrillation induction feature illustrated in FIGS. 5A and 5B will be described with reference to an embodiment where programming device 30 substantially controls the operation of the induction feature.

Upon receiving a command requesting the defibrillator induction feature via user interface 116, processor 110 configures defibrillator 12 for a fibrillation induction effectiveness test. Specifically, processor 110 selects an induction protocol and values for parameters of the selected induction protocol for defibrillator to use to induce fibrillation, a detection algorithm to detect an induced fibrillation, and a therapy progression to treat an induced fibrillation (130).

Processor 110 selects an induction protocol and parameter values for the selected protocol based on information stored in memory 118. The information relates to a plurality of protocols, and can indicate potential values or ranges of potential values for parameters of the protocols. For example, processor 110 can select T-wave shock as the initial induction protocol, with 0.6 Joules and midline of T-wave timing as the selected values for the parameters of the T-wave shock induction protocol. The information may indicate an order in which protocols or parameter values should be selected or modified.

One technique used to determine whether defibrillator 12 is effective in terminating fibrillation is to determine whether a defibrillation pulse delivered by defibrillator 12 with an energy level that is a safety margin, e.g., 10 Joules, below the maximum energy level available from defibrillator 12 is successful in defibrillating heart 14. If the safety margin pulse is effective, it is assumed that defibrillator 12 will likely be successful in terminating all fibrillations by resorting to the maximum level of defibrillator 12, if necessary.

Processor 110 interrogates defibrillator 12 via telemetry circuit 112 to determine its maximum output, or the maximum output of defibrillator 12 can be stored in memory 118. The safety margin is stored in memory 118, or provided by the user. Processor 110 selects a therapy progression that includes a first pulse delivered at an energy level which is the safety margin below the maximum output, and a second pulse at the maximum output. Processor 110 selects a simple single-zone fibrillation detection algorithm for the initial fibrillation detection algorithm.

Via telemetry circuit 112, processor 110 programs defibrillator 12 with the selected detection algorithm and treatment progression, and controls defibrillator 12 to attempt to induce fibrillation according to the selected induction protocol and parameter values (132). Processor 110 receives an indication from defibrillator 12 whether fibrillation is detected in response to the induction attempt (134). Defibrillator 12 indicates failure of the attempt, or processor 110 determines failure of the induction attempt upon timeout of a counter after the attempt without defibrillator 12 indicating induced fibrillation.

In some cases, fibrillation is induced, but not detected by defibrillator 12. The user monitoring the induction attempt will respond by manually defibrillating heart 14. In such cases, the user indicates to processor 110 that an undetected fibrillation occurred via user interface 116 (136). Processor 110 modifies the detection algorithm in response to undetected fibrillation, for example, by programming defibrillator 12 to detect fibrillation with an increased detection zone or multiple detection zones, change the sensitivity threshold for R-wave detection, or select a different combination of electrodes 40-50 and 58 for use in detecting the electrogram signal that is processed to detect fibrillation (138). When the detection algorithm is modified, processor 110 controls defibrillator 12 to again attempt to induce fibrillation according to the selected protocol and parameter values. In some embodiments, programmer 30 detects fibrillation via a surface electrogram in conjunction with information telemetered from defibrillator 12 to permit testing of defibrillation therapy where defibrillator 12 is having difficulty automatically detecting fibrillation.

If the induction attempt fails, processor 110 determines whether modifications to the parameter values for the selected induction protocol are available based on information stored in memory 118 (140). In some embodiments, memory 118 includes a limited set of modifications to be made to the protocol, or may include a threshold number of modifications that can be made per protocol. If modifications are available, processor 110 modifies one or more parameters for the protocol (142). If no modifications are available, processor 110 selects a different induction protocol and values for parameters of the different protocol based on information in memory 118 (144).

Processor 110 controls defibrillator 12 to attempt to induce fibrillation using the modified or newly selected protocol. For example, where a T-wave shock fails to induce fibrillation, processor 110 can control defibrillator 12 deliver another T-wave shock with modified energy level or timing, or can control defibrillator 12 to deliver a high-frequency pulse train. Processor 110 makes modifications and selects a new protocol until fibrillation is induced, or the protocols and modifications to those protocols are exhausted.

When fibrillation is induced, defibrillator 12 delivers therapy according to the progression (146). If first pulse with an energy level the safety margin below the maximum output of defibrillator 12 terminated the fibrillation, which indicates that defibrillator 12 is effective to treat fibrillation of patient 16, the test is complete and the user may use programmer 30 to program the device for permanent operation (156). If neither defibrillation pulse terminates the fibrillation (150), processor 110 alerts the user, for example, by activating alarm 120, so that the user can manually terminate the fibrillation (152).

If the second pulse needed to be delivered by defibrillator 12 to terminate the fibrillation (150), the test indicates that defibrillator 12 is not sufficiently effective in treating fibrillation as currently configured. Processor 110 can prompt the user via user interface 116 to change the configuration of defibrillator 12, and/or parameters of the defibrillation pulses delivered by defibrillator 12, to improve its effectiveness (154). For example, the user can adjust lead positions, select a different combination of electrodes 58 and 62-66 for use to deliver defibrillation pulses, or can select a different waveform for the pulses, e.g., switch between monophasic, biphasic and triphasic pulses. When the changes made by the user are complete, processor controls defibrillator 12 to again attempt induction with the previously successful protocol and parameter values.

The user can activate the defibrillator induction feature more than one time for patient 12, for example, to establish and then confirm the effectiveness of the defibrillator in detecting and treating fibrillation. For example, depending on the size of the safety margin or the magnitude of the first pulsed, the user may decide that it would be appropriate to have two successful terminations of ventricular fibrillation before deciding that defibrillator 12 is effective in detecting and terminating ventricular fibrillations.

Various embodiments of the invention have been described. For example, devices, such as an implanted defibrillator and a programming device, that provide a self-automated defibrillator induction feature have been described. However, one skilled in the art will appreciate that the invention is not limited to the described embodiments, and that various modifications can be made to the described embodiments without departing from the scope of the claims.

For example, an external defibrillator, such as an automatic external defibrillator (AED), can provide a self-adapting defibrillator induction feature according to the invention. AEDs are increasingly provided to patients that experience episodes of ventricular fibrillation for use at their homes. A self-adapting defibrillator induction feature as described herein can be provided to a user by the AED via a user interface of the AED. The AED can induce fibrillation according to a plurality protocols, modify values of parameters of the protocols, detect fibrillation, and deliver a therapy progression, as described herein. These and other embodiments are within the scope of the following claims.

The invention claimed is:

1. A method for monitoring an implantable medical device, comprising:
    automatically selecting a first fibrillation induction protocol defined by a first set of parameters for inducing fibrillation using a first induction technique and a value for a first parameter of the first fibrillation induction protocol;
    attempting to induce fibrillation of a heart according to the selected first protocol and first parameter value;
    determining whether fibrillation was induced according to the selected first protocol and the selected first parameter value;
    automatically modifying the first parameter value based on the determination;
    attempting to induce fibrillation of the heart according to the selected first protocol and the modified first parameter value;
    determining whether fibrillation was induced according to the selected first protocol and the modified first parameter value; and
    automatically selecting a second induction protocol defined by a second set of parameters for inducing fibrillation using a second induction technique different than the first induction technique and a value for a second parameter of the second induction protocol in response to determining that fibrillation was not induced according to the first protocol.

2. The method of claim 1, wherein the first protocol is one of T-wave shock delivery, pulse-train delivery, and direct current delivery, and the second protocol is another of T-wave shock delivery, pulse train delivery and direct current delivery, different than the first protocol.

3. The method of claim 1, further comprising attempting to induce fibrillation according to the second induction protocol and the selected second parameter value for the second induction protocol.

4. The method of claim 1, wherein selecting the second induction protocol comprises:
    determining that a threshold number of modifications to the first parameter value of the first protocol is met; and
    selecting the second induction protocol in response to the determination.

5. The method of claim 1, further comprising:
    automatically determining a progression of defibrillation therapies; and
    programming a defibrillator to deliver defibrillation therapy according to the determined progression in response to detection of an induced fibrillation.

6. The method of claim 5, wherein automatically determining the progression comprises determining a maximum defibrillation pulse energy level for a defibrillator, and wherein the progression includes a first defibrillation pulse at a safety margin below the maximum defibrillation pulse energy level and a second defibrillation pulse at the maximum defibrillation pulse energy level.

7. The method of claim 6, further comprising:
    determining that defibrillation has not occurred in response to delivery of the second defibrillation pulse; and
    indicating inability to defibrillate to a user based on the determination.

8. The method of claim 6, further comprising:
    determining that defibrillation has not occurred in response to delivery of the first defibrillation pulse; and
    prompting a user to change at least one of the configuration of the defibrillator and a parameter of the defibrillation pulses.

9. The method of claim 1, wherein determining whether fibrillation was induced comprises:
    automatically selecting a fibrillation detection algorithm; and
    programming a defibrillator to detect fibrillation according to the detection algorithm.

10. The method of claim 9, the method further comprising:
    receiving an indication from a user that fibrillation was induced according to the selected first protocol and the first parameter value but was not detected by the defibrillator according to the first detection algorithm; and
    modifying the detection algorithm in response to receiving the indication.

11. The method of claim 1, wherein automatically selecting the first fibrillation induction protocol and the value for the first parameter of the first fibrillation induction protocol comprises automatically selecting the first fibrillation induction protocol and the value for the first parameter of the first fibrillation induction protocol upon receiving a single command from a user.

12. The method of claim 1, wherein attempting to induce fibrillation comprises attempting to induce fibrillation of ventricles of the heart.

13. A medical device system comprising:
    a defibrillator;
    a memory to store information relating to a plurality of fibrillation induction protocols; and
    a processor to select one of the plurality of fibrillation induction protocols as a first induction protocol defined by a first set of parameters for inducing fibrillation using a first induction technique and a value for a first parameter of the first fibrillation induction protocol based on the information, control the defibrillator to attempt to induce fibrillation of a heart according to the first selected protocol and the first parameter value, determine whether fibrillation was induced according to the selected first protocol and the first parameter value, modify the first parameter value based on the determination, attempt to induce fibrillation of the heart according to the selected first protocol and the modified first parameter value, determine whether fibrillation was induced according to the selected first protocol and modified first parameter value, and automatically select a second induction protocol defined by a second set of parameters for inducing fibrillation using a second induction technique different than the first induction technique and a value for a second parameter of the second induction protocol in response to determining that fibrillation was not induced according to the first protocol.

14. The system of claim 13, wherein the first protocol is one of T-wave shock delivery, pulse-train delivery, and direct current delivery, and the second protocol is another of T-wave shock delivery, pulse train delivery and direct current delivery, different than the first protocol.

15. The system of claim 13, wherein the processor controls the defibrillator to attempt to induce fibrillation according to the second induction protocol and the selected second parameter value for the second induction protocol in response to determining that fibrillation was not induced according to the first induction protocol.

16. The system of claim 13, wherein the processor determines that a threshold number of modifications to the first parameter value of the first protocol is met, and selects the second induction protocol in response to the determination.

17. The system of claim 13, wherein the processor determines a progression of defibrillation therapies, and programs the defibrillator to deliver defibrillation therapy according to the determined progression in response to detection of an induced fibrillation.

18. The system of claim 17, wherein the processor determines a maximum defibrillation pulse energy level for the defibrillator, and
wherein the progression includes a first defibrillation pulse a safety margin below
the maximum defibrillation pulse energy level and a second defibrillation pulse at
the maximum defibrillation pulse energy level.

19. The system of claim 18, wherein the processor determines that defibrillation has not occurred in response to delivery of the second defibrillation pulse, and indicates inability to defibrillate to a user based on the determination.

20. The system of claim 18, wherein the processor determines that defibrillation has not occurred in response to delivery of the first defibrillation pulse, and prompts a user to change at least one of the configuration of the defibrillator and a parameter of the defibrillation pulses.

21. The system of claim 13, wherein the processor selects a fibrillation detection algorithm, and programs the defibrillator to detect fibrillation according to the detection algorithm.

22. The system of claim 21, wherein the processor receives an indication from a user that fibrillation was induced according to the selected first protocol and the first parameter value but was not detected by the defibrillator according to the first detection algorithm, and modifies the detection algorithm in response to receiving the indication.

23. The system of claim 13, wherein the processor selects one of the plurality of fibrillation induction protocols as the first induction protocol and the value for the first parameter of the first fibrillation induction protocol in response to receiving a single command from a user.

24. The system of claim 13, wherein the processor is included in one of the defibrillator and a programming device.

25. The system of claim 13, wherein the defibrillator is an implanted defibrillator.

26. The system of claim 13, wherein the processor controls the defibrillator to attempt to induce fibrillation of ventricles of the heart.

27. A computer-readable medium comprising instructions that cause a processor of a defibrillator to:
select a first fibrillation induction protocol defined by a first set of parameters for inducing fibrillation using a first induction technique and a value for a first parameter of the first fibrillation induction protocol;
control the defibrillator to attempt to induce fibrillation of a heart accor to the selected first protocol and the first parameter value;
determine whether fibrillation was induced according to the selected first protocol and the first parameter value;
modify the first parameter value based on the determination; attempt to induce fibrillation of the he
protocol and the modified first parameter value; determine whether fibrillation was induced according to the selected first
protocol and modified first parameter value; and
automatically select a second induction protocol defined by a second set of parameters for inducing fibrillation using a second induction technique different than the first induction technique and a value for a second parameter of the second induction protocol in response to determining that fibrillation was not induced according to the first protocol.

28. The computer-readable medium of claim 27, wherein the first protocol is one of T-wave shock delivery, pulse-train delivery, and direct current delivery, and the second protocol is another of T-wave shock delivery, pulse train delivery and direct current delivery, different than the first protocol.

29. The computer-readable medium of claim 27, the medium further comprising instructions that cause the processor to-control the defibrillator to attempt to induce fibrillation according to the second induction protocol and the selected second parameter value for the second induction protocol.

30. The computer-readable medium of claim 29, wherein the instructions that cause the processor to select the second induction protocol comprise instructions that cause the processor to:
determine that a threshold number of modifications to the first parameter value of the first protocol is met; and
select the second induction protocol in response to the determination.

31. The computer-readable medium of claim 27, further comprising instructions that cause the processor to:
determine a progression of defibrillation therapies; and
program the defibrillator to deliver defibrillation therapy according to the determined progression in response to detection of an induced fibrillation.

32. The computer-readable medium of claim 31, wherein the instructions that cause the processor to determine the progression of defibrillation therapies comprise instructions that cause the processor to determine a maximum defibrillation pulse energy level for the defibrillator, and
wherein the progression includes a first defibrillation pulse a safety margin below the maximum defibrillation pulse energy level and a second defibrillation pulse at the maximum defibrillation pulse energy level.

33. The computer-readable medium of claim 32, further comprising instructions that cause the processor to:
determine that defibrillation has not occurred in response to delivery of the second defibrillation pulse; and
indicate inability to defibrillate to a user based on the determination.

34. The computer-readable medium of claim 32, further comprising instructions that cause the processor to:
determine that defibrillation has not occurred in response to delivery of the first defibrillation pulse; and
prompt a user to change at least one of the configuration of the defibrillator and a parameter of the defibrillation pulses.

35. The computer-readable medium of claim 32, further comprising instructions that cause the processor to:
   select a fibrillation detection algorithm; and
   program the defibrillator to detect fibrillation according to the detection algorithm.

36. The computer-readable medium of claim 35, further comprising instructions that cause the processor to:
   receive an indication from a user that fibrillation was induced according to the selected first protocol and the first parameter value but was not detected by the defibrillator according to the first detection algorithm; and
   modify the detection algorithm in response to receiving the indication.

37. The computer-readable medium of claim 27, wherein the instructions that cause the processor to select the first fibrillation induction protocol comprise instructions that cause the processor to select the first fibrillation induction protocol in response to receiving a single command from a user.

* * * * *